United States Patent [19]

Wideman et al.

[11] 4,308,211

[45] Dec. 29, 1981

[54] PROCESS FOR THE PREPARATION OF ANTHRAQUINONE

[75] Inventors: Lawson G. Wideman, Tallmadge; Lynn A. Bente, Dover, both of Ohio

[73] Assignee: The Goodyear Tire & Rubber Company, Akron, Ohio

[21] Appl. No.: 220,885

[22] Filed: Dec. 29, 1980

[51] Int. Cl.$^3$ .............................................. C07C 50/18
[52] U.S. Cl. ................................................... 260/369
[58] Field of Search ......................................... 260/369

[56] References Cited

U.S. PATENT DOCUMENTS

| | | | |
|---|---|---|---|
| 3,150,930 | 9/1964 | Hiratsuka et al. | 260/369 |
| 3,670,034 | 6/1972 | Robinson | 260/369 |
| 4,152,340 | 5/1979 | Delavarenne et al. | 260/369 |

Primary Examiner—Winston A. Douglas
Assistant Examiner—Raymond K. Covington
Attorney, Agent, or Firm—D. O. Nickey

[57] ABSTRACT

A process for the preparation of anthraquinone from 1, 4, 4a, 5, 8, 8a, 9a, 10a-octahydroanthraquinone (OHAQ) which comprises contacting OHAQ as a melt with a catalyst.

5 Claims, No Drawings

PROCESS FOR THE PREPARATION OF ANTHRAQUINONE

TECHNICAL FIELD

The present invention relates to a process for the preparation of anthraquinone.

BACKGROUND ART

It is known from the prior art that anthraquinone may be obtained on heating with air or oxygen a solution or dispersion of octahydro-anthraquinone (French Pat. No. 673,825 of Apr. 22, 1929). Another process comprises heating 1, 4, 4a, 9a-tetrahydro-anthraquinone in the presence of nitrobenzene (British Pat. No. 895,620 of May 2, 1962). It is also possible to obtain anthraquinone by heating the 1, 4, 4a, 5, 8, 8a, 9a, 10a-octahydroanthraquinone in the presence of nitrobenzene, but the yield of the reaction is poor and the product obtained is not pure.

In addition, U.S. Pat. No. 4,152,340 discloses the production of anthraquinone by reacting 1, 4, 4a, 5, 8, 8a, 9a, 10a-octahydro-anthraquinone with nitrobenzene in the presence of a catalytic amount of a basic compound soluble in the reaction medium and an inhibitor of free radical reactions.

Those skilled in the art are constantly searching for new methods of preparation of anthraquinone due to this compound's versatility, however, none of the patents cited or other literature discloses or suggests a process in which a solvent is not employed nor is the use of a basic compound or inhibitor.

In addition, presently accepted methods of synthesis in the prior art discloses complex and costly separation and purification procedures which are not needed in the process of the present invention.

The inventors have made extensive investigations in an attempt to provide an improved process which can overcome the various disadvantages in the prior art suggestions and can separate and recover high purity anthraquinone in high yields by an industrially advantageous operation. These investigations finally led to the discovery that the various defects of the prior art can be overcome and high purity anthraquinone can be separated and recovered in high yields by an industrially advantageous operation.

The present invention encompasses an approach to anthraquinone by the catalytic dehydrogenation rather than the direct oxidation of octahydro-anthraquinone (OHAQ) intermediate or other intermediates. OHAQ is the reaction product of two molar equivalents of 1, 3-butadiene with one molar equivalent of benzoquinone and has the following structure:

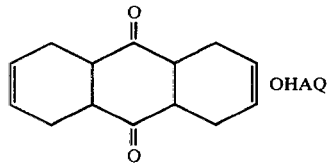
OHAQ (I)

To a chemist skilled in this particular art an acceptable approach would appear to be the dehydrogenation of OHAQ in the vapor phase by a continuous reaction over a fixed bed catalyst system. No solvent would be employed and the OHAQ would be metered into the system as a melt. This approach attempted by the applicants using several catalyst systems produced only traces of anthraquinone and the main reaction product as shown by mass spectroscopy, gas chromatography, NMR and IR analysis was anthracene with a melting point of 216° C. The dehydrogenation is accompanied by dehydration over a palladium on an aluminum oxide carrier that gives an 83 percent yield of anthracene plus water according to the following reaction scheme:

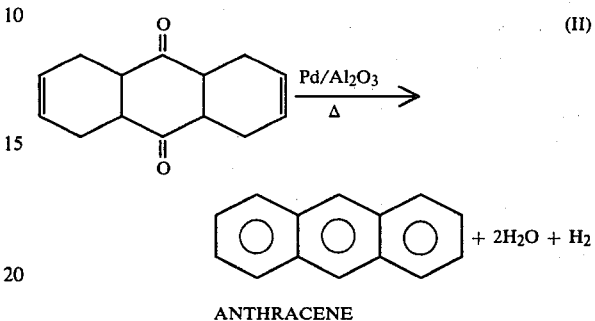

ANTHRACENE

In an attempt to overcome this undesirable reaction more inert catalysts were experimented with in the vapor phase. Low surface area alumina ($Al_2O_3$) and $Na_2CO_3/Al_2O_3$ gave anthracene as the major product, but also gave a complicated mixture of partially dehydrogenated and dehydrated products. Lower reaction temperatures were also attempted (less than 325° C.) but would not properly vaporize products from the reactor system.

Attempts to use a solvent to moderate the reaction produced a variety of products that were dependent on the reaction conditions. The use of hydrogen acceptors in the solvent system did not appreciably improve the production of anthraquinone.

Liquid phase reactions of OHAQ without a solvent were carried out with OHAQ as a melt. The OHAQ and powdered catalysts were intimately mixed under nitrogen and heated above the melting point of OHAQ. When the catalyst was 5% palladium/carbon (Pd/C) a pronounced exotherm was observed near 230° C. This exotherm is believed to be the heat of reaction of the isomerization of OHAQ to isomerized OHAQ (i-OHAQ) according to the following chemical structures:

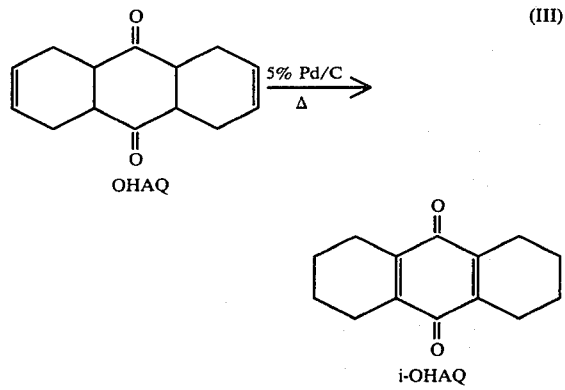

Mass spectrum and NMR analysis of the product from this reaction showed that i-OHAQ to be an isomer of OHAQ and also indicated the absence of olefinic protons. The isolated i-OHAQ was then reacted at 273°

C. in the presence of a 5% palladium/carbon catalyst to affect the conversion to anthraquinone according to the following scheme:

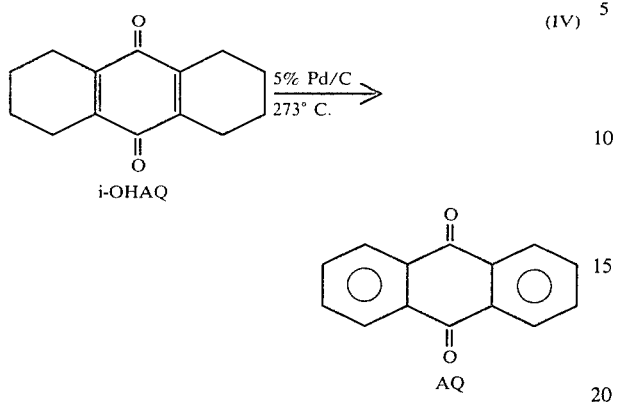

The conversion of OHAQ to isomerized OHAQ is not without the formation of another intermediate product which is the isomer of tetrahydro-anthraquinone (THAQ):

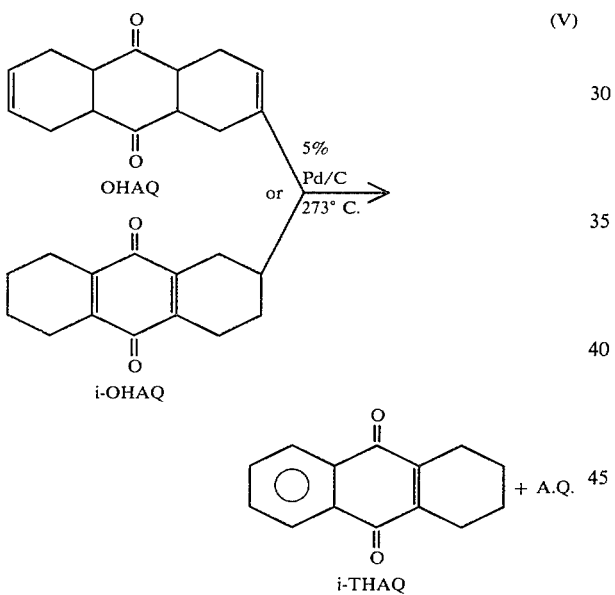

The molecular weight of i-THAQ was verified by mass spec and the NMR analysis spectrum showed no olefin protons. A crude mixture of i-OHAQ and i-THAQ, approximately 1 to 1, gave a very similar yield of AQ which was obtained under the identical reaction conditions used to convert OHAQ to AQ but at a lower temperature, approximately 250° C.

This fact suggests that the by-products, i-OHAQ and i-THAQ can be recycled.

This initial investigation also determined unexpectedly that the length of time that the melt reaction is held at or near 300° C. has a pronounced effect on the yield of anthraquinone.

Other catalysts, such as rhodium, Rh/C and cobalt produce very little anthraquinone from OHAQ but gives high yields of the isomerized OHAQ. In addition, it was determined that used catalysts from a typical Rh/C run with OHAQ can be recycled to give almost identical results.

Tetrahydro-naphthoquinone (THNQ) is quite often an impurity in the preparation of OHAQ and it was determined that a 1 to 1 mixture of OHAQ and THNQ gave acceptable yields of anthraquinone and naphthoquinone when short reaction times were employed after the initial exotherm of the melt.

DISCLOSURE OF THE INVENTION

There is disclosed a process for the preparation of anthraquinone which is characterized by (1) contacting 1, 4, 4a, 5, 8, 8a, 9a, 10a-octahydro-anthraquinone as a melt with (2) a catalyst at a ratio of no greater than 10,000 to 1 by weight of OHAQ to catalyst; (3) said catalyst being selected from the group consisting of Group 8 metals of the Periodic Table, oxides thereof, and Group 8 metals of the Periodic Table or oxides thereof supported on an inert carrier; (4) at a temperature not greater than 330° C.; (5) for no longer than 10 minutes; (6) separating the anthraquinone from the undesirable by-products. The undesirable reaction products and intermediates can be recycled back to the reaction vessel.

The applicants have found that it is possible to significantly improve the yield of anthraquinone by reacting 1, 4, 4a, 5, 8, 8a, 9a, 10a -octahydro-anthraquinone (OHAQ) as a melt with a finely dispersed form of a metal catalyst; wherein the contact time of the OHAQ with the catalyst and the ratio to OHAQ to catalyst is a major factor in the ratio of anthraquinone to 1, 2, 3, 4-tetrahydro-anthraquinone (i-THAQ) and 1, 2, 3, 4, 5, 6, 7, 8-octahydro-anthraquinone (i-OHAQ) and anthracene.

The octahydro-anthraquinone (OHAQ) reaction is initially a highly exothermic and is immediately followed by the rapid elimination of hydrogen which has a pronounced cooling effect on the reaction system. Reaction times of less than 1 minute past the exotherm with a rhodium on carbon catalyst provided yields of 62 percent anthraquinone, along with isomerized OHAQ and isomerized THAQ. If the same reaction is conducted with palladium on a carbon support, a 75 percent yield of anthraquinone is obtained along with the isomerized OHAQ and isomerized THAQ. The reaction can be visualized to be the following:

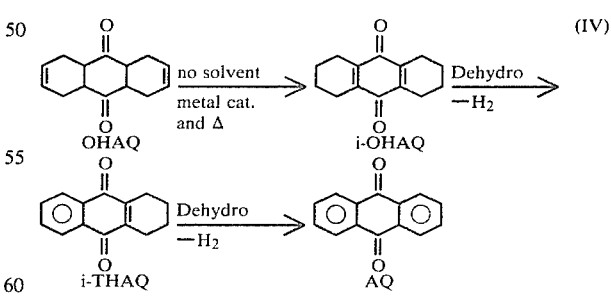

The reaction can be carried out at a temperature from about 200° C. to 330° C. and preferably from about 290° C. to 310° C.

The concentration of octahydro-anthraquinone in the reaction medium may vary within large limits. For reasons of productivity it is preferable to have over 40 percent by weight.

The process of the present invention may be conducted at subatmospheric conditions, however, no benefit is realized and temperature control becomes more difficult.

Various compounds can be used according to the invention as catalytic agents as long as they are capable of isomerization and dehydrogenation of the starting material without dehydration. Preferred Group 8 metals of the Periodic Table that are useful in the process of the present invention are palladium, rhodium, ruthenium and oxides of these metals with or without being placed upon an inert carrier. The ratio of catalyst to OHAQ in the reaction melt should be less than 1 to 10,000. Much higher amounts could be used if desired but there is no economic reason to do so.

By means of the process according to the invention it is possible to reduce considerably the formation of the undesired product anthracene in the preparation of anthraquinone. Furthermore, the separation of the reaction products can be carried out with greater freedom from problems since troublesome high boiling compounds and other undesirable reaction products are produced in smaller quantity.

A further advantage represented by the process of the invention resides in that all reaction separation operations can be carried out in a variety of methods. Hence, the operation of anthraquinone manufacture is particularly simple from a technical point of view.

The following examples are provided to illustrate and not to limit the scope of the present invention.

EXAMPLE 1

The reaction vessel consists of a 100 milliliter flask fitted with a nitrogen inlet and an air cooled condenser with a gas vent. 5 grams of OHAQ and 0.1 grams of 5% Pd/C catalyst were intimately mixed under nitrogen and heated above the melting point of OHAQ. When the reaction temperature is near 200°–230° C., an exotherm develops and the heating source is adjusted so that the temperature is maintained at 300° C. for 10 minutes. A rapid evolution of gas is observed at 300° C. The reaction mixture is allowed to cool to room temperature and then dissolved in approximately 400 milliliters of hot acetone and filtered. The acetone was allowed to evaporate and gas chromatograph analysis was used to determine the concentration of anthraquinone.

EXAMPLES 2–8

The procedure of Example I was followed except that the time the reaction mixture was held at 300° C. was varied. The analysis of the reaction product from Example I–VIII is set out in Table I.

TABLE I

| | 0.1 gms. of 5% Pd/C Catalyst with 5 gms. OHAQ as a Melt | | | |
|---|---|---|---|---|
| Example No. | Residence Time at 300° C. Mins. | A.Q. Yield | i-OHAQ i-THAQ | Anthracene And Others |
| 1 | 10 | 75% | 20% | 5% |
| 2 | 20 | 28% | 29% | 43% |
| 3 | 30 | 14% | 18% | 68% |
| 4 | 10 (30 sec. cool to ambient temp.) | 71% | 23% | 6% |
| 5 | 1 | 72% | 24% | 4 |
| 6 | 1 (30 sec. cool to ambient temp.) | 72% | 24% | 4 |

TABLE I-continued

| | 0.1 gms. of 5% Pd/C Catalyst with 5 gms. OHAQ as a Melt | | | |
|---|---|---|---|---|
| Example No. | Residence Time at 300° C. Mins. | A.Q. Yield | i-OHAQ i-THAQ | Anthracene And Others |
| 7 | 1/60 | 71% | 26% | 3 |
| 8 | 1/60 (30 sec.) cool to ambient temp.) | 68% | 28% | 4 |

It has been found by the applicants that conversion levels of approximately 60–75% AQ are desirable since it is easier to separate the very insoluble A.Q. and recycle the partially reacted intermediates over the same catalyst, than to push the reaction beyond approximately 20 minutes of reaction time, as water elimination becomes appreciable and anthracene becomes a major product.

EXAMPLES 9–13

The reaction vessel, reaction conditions and starting materials are the same as in Example I, but 0.1 gms. of 5% Rh/C catalyst was used and the reaction time and temperature were varied. The results are set out in the following Table:

TABLE II

| | 5.0 gms. OHAQ as a Melt with 0.1 gms. of 5% Rh/C Catalyst | | | | |
|---|---|---|---|---|---|
| Example No. | Reaction Temp. °C. After Attaining Exotherm at 300° C. | Reaction Time After Exotherm (min.) | A.Q. Yield % | i-OHAQ i-THAQ Yield | Anthracene & Others |
| 9 | 300 | 60 | 26 | 4 | 70 |
| 10 | 275 * | 60 | 47 | 13 | 40 |
| 11 | 250 * | 60 | 36 | 19 | 45 |
| 12 | 200 * | 60 | 40 | 27 | 33 |
| 13 | 25 * | 1 | 60 | 28 | 12 |

* After attaining 300° C., then reaction cooled and maintained at this temperature.

0.01 gms. of used catalyst from Example 13 (Rh/C) was recycled with fresh OHAQ (5 gms OHAQ/0.01 gms. of 5% Rh/C catalyst) and gave under the reaction conditions of Example 13 results almost identical to Example 13. If the reaction heater is removed as the exotherm pushes the temperature past 300° C. with immediate cooling, the one-pass yield of A.Q. is improved. The previous data indicates that extended reaction times are not desirable.

To show the effect of the carrier or support in the catalyst systems the following Examples are provided:

EXAMPLE 14 AND 15

The reactor and the reaction conditions are as in Example 1 but the catalyst support was changed. The following Table sets out the data collected.

TABLE III 5 gms OHAQ as Melt With 0.1 gms. of Catalyst

| Example No./ Catalyst System | Reaction temp. After Attaining 300° C. cooled Maintained at °C. | Reaction time After Exotherm (min.) | A.Q. Yield % | i-OHAQ i-THAQ Yield | Anthracene & Others |
|---|---|---|---|---|---|
| 14 5% Pd/C | 25 | 1 | 75 | 20 | 5 |
| 15 0.5% Pd/Al₂O₃ (*1.0 gm. of cat. used) | 300 | 10 | 72 | 23 | 2 |

The data indicates and a skilled chemist would expect the carrier or support upon which the Group 8 metals of the Periodic Table is dispersed has little or no effect in the process of the present invention.

The following Examples are presented to illustrate that other Group VIII metals and oxides of those metals are effective as catalysts in the process of the present invention:

EXAMPLE 16

The reaction and the reaction conditions are set out in Example 1 except that different catalysts were used and the reaction temperature was increased to 330° C.

TABLE IV 5 gms. of OHAQ as Melt With 0.1 gms. of Catalyst

| Example No/ Catalyst System | Reaction Temp. | Reaction Time at Temp. (Min.) | A.Q. Yield | i-OHAQ i-THAQ Yield | Anthracene & Others |
|---|---|---|---|---|---|
| 16 Ni/SiO₂ | 330° C. | 10 | 44 | 43 | 13 |
| 17 Co/SiO₂ | 330° C. | 10 | 14 | 83 | 2 |
| 18 NiO | 330° C. | 10 | 53 | 45 | 2 |
| 19 Fe₂O₃/Al₂O₃ | 330° C. | 10 | 28 | 62 | 2 |

The data contained in Table IV illustrates that other Group 8 metals of the Periodic Table and their oxides can be used in the process of the present invention. The increase in reaction temperature at 330° C. was required to effect hydrogen evolution due to the catalysts lesser activity.

To illustrate the boundaries of catalysts to OHAQ ratios the following Examples are presented.

EXAMPLES 20-22

The reaction and reaction conditions are set out as in Example 1 except that the ratio of catalyst to OHAQ was varied. The data is presented in Table V.

TABLE V

5 Gms. OHAQ as a Melt With From 0.1 to 0.001 Gms. of 5% Pd/C

| Example No./Amt. Catalyst | Residence Time at Temp. | Reaction Temp. | A.Q. Yield | i-OHAQ i-THAQ Yield | Anthracene & Others |
|---|---|---|---|---|---|
| 1 0.1 gms. | 10 | 300° C. | 75 | 20 | 5 |
| 20 0.01 gms. | 10 | 300° C. | 51 | 47 | 2* |
| 21 0.005 gms. | 10 | 300° C.-330° C. | trace | 96 | 2 |
| 22 0.001 gms. | 20 | 300° C.-330° C. | trace | 96 | 4 |

*This Example is a 10,000 to 1 OHAQ to catalyst ratio.

The data contained in Table V demonstrates that ratios of greater than 10,000 to 1 OHAQ to Group 8 metals of the Periodic Table by weight is not effective or economical. The applicants have determined that higher OHAQ to Group 8 metals of the Periodic Table ratios function but there is no economical or practical reason to do so.

Applicants have investigated several methods to separate the A.Q. from the reaction mixture and have found acetone and toluene and pentane/chloroform to be satisfactory solvents to effect A.Q. removal from the reaction mixture. A skilled chemist will be readily able to suggest other solvents and recrystallization techniques. Applicants feel that steam distillation of the reaction mixture might provide an industrially acceptable means for separation. Additionally, once the A.Q. has been separated from the reaction mixture the reaction intermediates, i-OHAQ and i-THAQ along with anthracene, may be recycled to the reaction vessel.

Applicants have also found that the process of the present invention can be used when starting with OHAQ that has contained within it tetrahydronaphoquinone.

While certain representative embodiments and details have been shown for the purpose of illustrating the invention, it will be apparent to those skilled in this art that various changes and modifications may be made therein without departing from the spirit or scope of the invention.

We claim:

1. A process for the preparation of anthraquinone which is characterized by:
    contacting, at a temperature not greater than 330° C. for no longer than ten minutes, 1, 4, 4a, 5, 8, 8a, 9a, 10a -octahydroanthraquinone (OHAQ) as a melt with a catalyst, the weight ratio of said OHAQ to said catalyst being no greater than 10,000 to 1, said catalyst being selected from the group consisting of group 8 metals of the Periodic Table or, oxides thereof unsupported on an inert carrier and Group 8 metals of the Periodic Table or oxides thereof supported on an inert carrier and separating the anthraquinone from the undesirable reaction products.

2. A process according to claim 1 wherein the undesirable reaction products and intermediates are recycled back to the reaction vessel.

3. A process according to claim 1 wherein the catalyst is palladium on a carbon support.

4. A process according to claim 2 wherein the reaction temperature is held at 310° C. for 5 minutes.

5. A process according to claim 1 wherein the catalyst is palladium on a carbon support and the reaction temperature is 300° C. for not more than 10 minutes.

* * * * *